US009867709B2

(12) United States Patent
Nocco et al.

(10) Patent No.: US 9,867,709 B2
(45) Date of Patent: Jan. 16, 2018

(54) PARTIAL UNICOMPARTMENTAL SYSTEM FOR PARTIAL KNEE REPLACEMENT

(71) Applicant: Active Implants LLC, Memphis, TN (US)

(72) Inventors: Emanuele Nocco, Memphis, TN (US); Eran Linder-Ganz, Tel Aviv (IL)

(73) Assignee: Active Implants, LLC, Memphis, TN (US)

( * ) Notice: Subject to any disclaimer, the term of this patent is extended or adjusted under 35 U.S.C. 154(b) by 30 days.

(21) Appl. No.: 15/003,482

(22) Filed: Jan. 21, 2016

(65) Prior Publication Data
US 2016/0206435 A1 Jul. 21, 2016

Related U.S. Application Data

(60) Provisional application No. 62/106,091, filed on Jan. 21, 2015.

(51) Int. Cl.
*A61F 2/08* (2006.01)
*A61F 2/38* (2006.01)
*A61F 2/30* (2006.01)

(52) U.S. Cl.
CPC .......... *A61F 2/3872* (2013.01); *A61F 2/3836* (2013.01); *A61F 2/3859* (2013.01); *A61F 2/3868* (2013.01); *A61F 2/30756* (2013.01); *A61F 2002/3895* (2013.01)

(58) Field of Classification Search
USPC .......... 623/14.12, 20.28, 20.29, 20.3, 20.33, 623/20.15, 20.35
See application file for complete search history.

(56) References Cited

U.S. PATENT DOCUMENTS 4,309,778 A * 1/1982 Buechel ................ A61F 2/3868
  623/20.29
4,344,193 A * 8/1982 Kenny .................. A61F 2/3872
  128/DIG. 21

(Continued)

FOREIGN PATENT DOCUMENTS

| EP | 2140839 (A1) | 1/2010 |
| WO | WO 2010/004342 (A2) | 1/2010 |
| WO | WO 2012/126496 (A1) | 9/2012 |

OTHER PUBLICATIONS

International Search Report and Written Opinion received in Patent Cooperation Treat Application No. PCT/US2016/014332, dated Aug. 4, 2016, 20 pages.

*Primary Examiner* — David H Willse
*Assistant Examiner* — Javier Blanco
(74) *Attorney, Agent, or Firm* — Haynes and Boone, LLP

(57) ABSTRACT

A prosthetic system for use as a partial unicompartmental artificial knee replacement system. In one form, an artificial femoral bearing component is implanted along with a floating meniscus component that is configured to cooperate with the femoral bearing component to move through a plurality of translational and rotational positions as the knee rotates through a variety of angles. In another form, an artificial tibial bearing component is implanted along with a floating meniscus component that is configured to cooperate with the tibial bearing component to move through a plurality of translational and rotational positions as the knee rotates through a variety of angles.

7 Claims, 20 Drawing Sheets

(56) References Cited

U.S. PATENT DOCUMENTS

| | | | | |
|---|---|---|---|---|
| 5,871,542 A | * | 2/1999 | Goodfellow | A61F 2/3868 623/20.16 |
| 6,206,927 B1 | * | 3/2001 | Fell | A61F 2/3872 623/14.12 |
| 6,264,697 B1 | * | 7/2001 | Walker | A61F 2/3886 623/20.14 |
| 6,946,001 B2 | * | 9/2005 | Sanford | A61F 2/3868 623/20.3 |
| 7,297,161 B2 | * | 11/2007 | Fell | A61F 2/38 623/14.12 |
| 8,192,491 B2 | * | 6/2012 | Fox | A61F 2/3872 623/14.12 |
| 8,361,147 B2 | | 1/2013 | Shterling et al. | |
| 9,381,089 B2 | | 7/2016 | Linder-Ganz et al. | |
| 2003/0055500 A1 | | 3/2003 | Fell et al. | |
| 2004/0006394 A1 | * | 1/2004 | Lipman | A61F 2/3868 623/20.29 |
| 2008/0243259 A1 | | 10/2008 | Lee et al. | |
| 2008/0243260 A1 | | 10/2008 | Lee et al. | |
| 2012/0136452 A1 | * | 5/2012 | Richter | A61F 2/3886 623/20.28 |
| 2012/0239158 A1 | * | 9/2012 | Wagner | A61F 2/38 623/20.21 |
| 2013/0103159 A1 | * | 4/2013 | Andriacchi | A61F 2/38 623/20.28 |
| 2014/0142713 A1 | | 5/2014 | Wright et al. | |

\* cited by examiner

PARTIAL UNICOMPARTMENTAL SYSTEM FOR PARTIAL KNEE REPLACEMENT

CROSS-REFERENCE TO RELATED APPLICATION

This application claims priority to U.S. Provisional Application No. 62/106,091, filed Jan. 21, 2015, which is hereby incorporated by reference in its entirety.

BACKGROUND

The present disclosure generally relates to medical prosthetic devices, systems, and methods. More specifically, in some instances the present disclosure relates to prosthetic devices that replace at least part of the functionality of the natural meniscus and knee bearing surfaces. Each knee has two menisci, a lateral meniscus and a medial meniscus. Each meniscus is a crescent-shaped fibrocartilaginous tissue attached to the tibia at an anterior and a posterior horn. Damage to the meniscus can cause pain and arthritis. Further, cartilage on the bearing surfaces of the tibia and femur may also become damaged, leading to additional pain and damage to the meniscus. Accordingly, it is current practice to perform a total knee replacement in many patients with damaged knee cartilage. Alternatively, if the damaged cartilage is limited to one side of the knee, a unicompartmental knee replacement procedure may be performed where the femur and tibial bones are milled off and implants are inserted into both bones to perform the bearing function of the knee. Even if cartilage of only one of the bone surfaces is damaged, both cartilage surfaces will be removed and replaced with an artificial bearing surface.

There remains a need for less traumatic and bone sparing devices that can accomplish load bearing and knee function through a range of knee motions. While existing devices, systems, and methods have attempted to address these issues, they have not been satisfactory in all respects. Accordingly, there is a need for the improved devices, systems, and methods in accordance with the present disclosure.

SUMMARY

In one embodiment, a partial unicompartmental knee replacement system is provided. The partial unicompartmental knee replacement system offers a system to allow treatment of only the effected joint surface while retaining the intact cartilage bearing surfaces on the opposing portions of the joint. In one form, the system includes a femoral component configured for resurfacing at least a portion of a femoral condyle, the femoral component having a first bearing surface with a first radius of curvature, a second bearing surface with a second radius of curvature and a third bearing surface with a third radius of curvature and a meniscus component, configured for placement between the femoral component and the natural tibia. The meniscus component floats in the knee joint between the natural tibia and the femoral component and has a first position in the knee joint when in contact with the first area, a second position in the knee joint when in contact with the second area and a third position in the knee joint when in contact with the third area. In one aspect, the first position is rotationally offset from at least one of the second and third positions. In a further aspect, the first position is longitudinally offset from at least one of the second and third positions. In still a further aspect, the first position is laterally offset from at least one of the second and third positions. In at least one form, the first radius of curvature is different than the third radius of curvature.

In a further form, a tibial bearing component may be implanted to replace the natural tibial bearing surface. The tibial bearing component includes a multi-faceted bearing surface with a convex bearing portion. A free floating meniscus device has a lower surface for engaging the tibial bearing component and an upper surface for engaging the natural femoral bearing surface. The meniscus device floats between a plurality of anterior to posterior, and rotational positions, in response to movement of the femur and engagement with the multi-faceted bearing surface of the tibial bearing component.

In another embodiment, a method is provided for replacing the function of a cartilage bearing surface and a meniscus within a joint. The method of replacing the bearing surface includes removing the cartilage surface from one bone in the joint and implanting a replacement bearing component. The method of replacing the meniscus function within a joint includes removing a portion of a meniscus within the joint and leaving intact a meniscus remnant, then inserting a free floating meniscus replacement implant into the joint and engaging the meniscus replacement implant with the meniscus remnant such that the meniscus replacement implant is at least in part retained within the joint by the meniscus remnant. In a further aspect, the meniscus replacement implant includes a retention channel within the sidewall of the implant and the method of engaging the meniscus replacement implant with the meniscus remnant includes aligning the retention channel with the meniscus remnant. In still a further feature, the retention channel is a retention channel formed in a posterior portion of a knee meniscus replacement implant and the engaging includes aligning the retention channel with a posterior portion of the meniscus remnant. In yet a further aspect, the engaging includes suturing a portion of the meniscus replacement implant to a portion of the meniscus remnant or to tissue of the joint capsule adjacent the joint.

BRIEF DESCRIPTION OF DRAWINGS

Other features and advantages of the present disclosure will become apparent in the following detailed description of embodiments of the disclosure with reference to the accompanying of drawings, of which.

DETAILED DESCRIPTION

Figure 1:
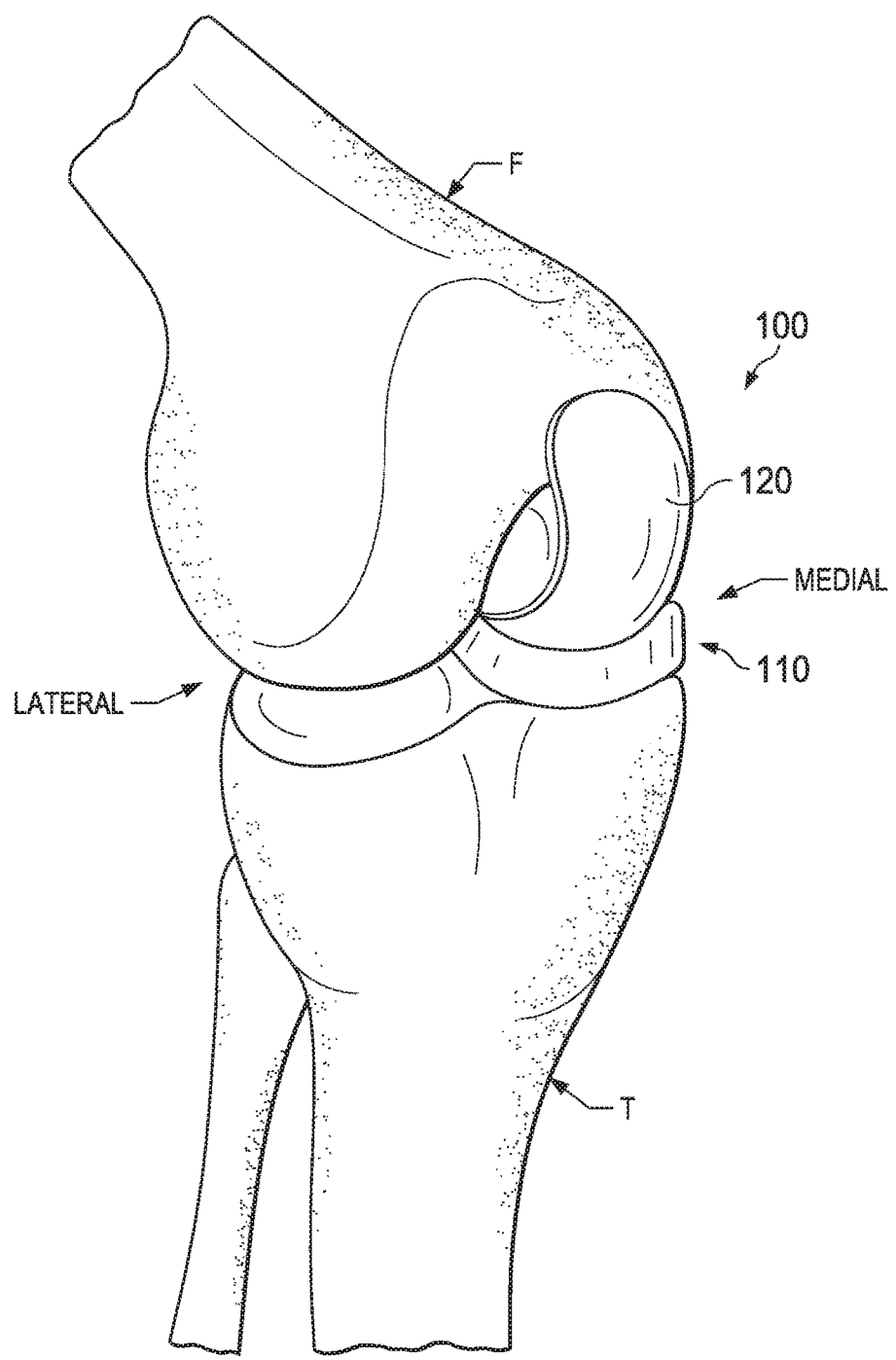
FIG. 1 is a diagrammatic perspective view of a right knee joint with a unicompartmental knee replacement according to one aspect of the present invention.

For the purposes of promoting an understanding of the principles of the present disclosure, reference will now be made to the embodiments illustrated in the drawings, and specific language will be used to describe the illustrated embodiments. It is nevertheless understood that no limitation of the scope of the disclosure is intended. Any and all alterations or modifications to the described devices, instruments, and/or methods, as well as any further application of the principles of the present disclosure that would be apparent to one skilled in the art are encompassed by the present disclosure even if not explicitly discussed herein. Further, it is fully contemplated that the features, components, and/or steps described with respect to one embodiment may be combined with the features, components, and/or steps described with respect to other embodiments of the present disclosure.

Figure 2:
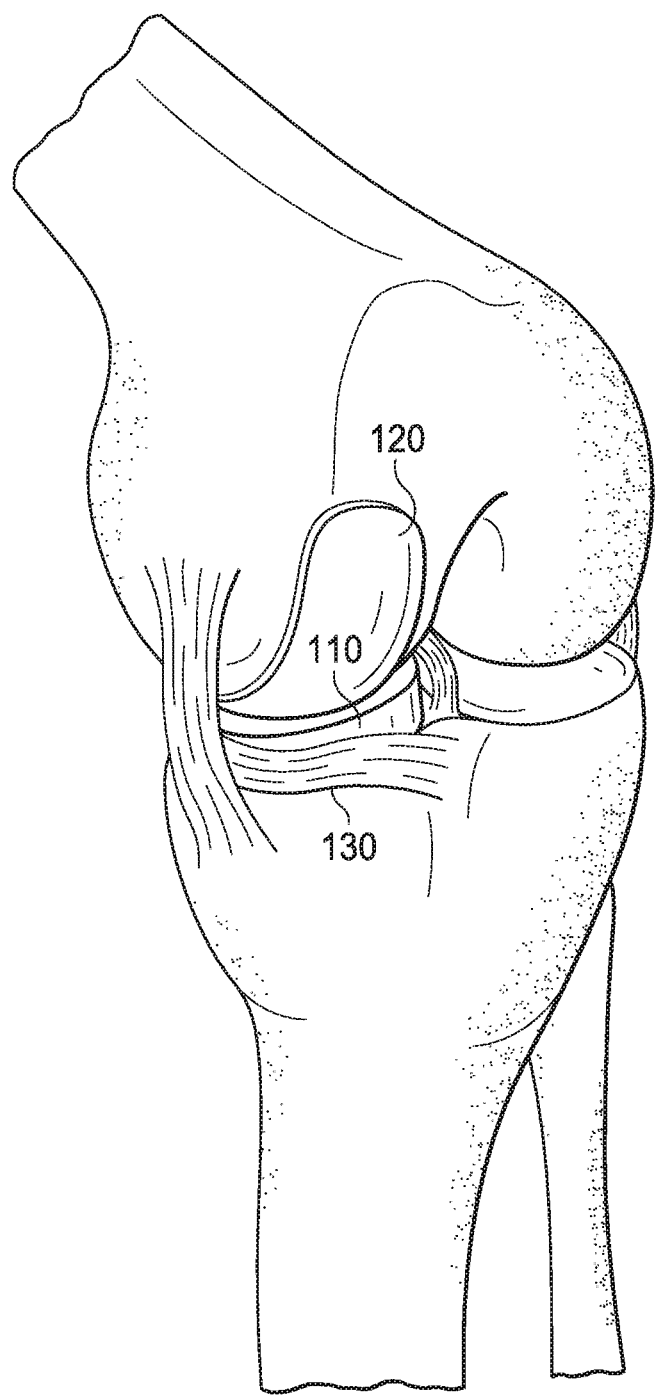
FIG. 2 is a diagrammatic partially exploded perspective view of a left knee joint with a unicompartmental knee replacement according to one aspect of the present invention.

Referring now to FIG. 1, there is shown a right knee joint between femur F and tibia T. A partial unicompartmental knee replacement (PUKR) system 100 has been implanted in the medial compartment of the knee. As will be explained in greater detail below, the PUKR system is only a partial unicompartmental knee replacement as it leaves intact at least one of the natural bearing surfaces of the knee. In the illustrated embodiment, an artificial femoral bearing surface 120 has been implanted on the femur to bear against a prosthetic meniscus device 110, which in turn bears against the native tibial plateau. A superior surface of the prosthetic meniscus device 110 is in contact with the artificial femoral bearing surface 120, and an inferior surface of the prosthetic meniscus device 110 is in contact with the natural tibial bearing surface. FIG. 2 illustrates that a similar system may be implanted in the left knee, including the prosthetic meniscus device 110 and the femoral bearing surface 120. The meniscus device 110 is positioned within the knee joint adjacent to a ligament 130, such as a coronary or meniscotibial ligament, a meniscofemoral ligament, and/or a transverse ligament. For illustrative purposes, the prosthetic system will be described in the following drawings in conjunction with a left knee, medial meniscus and bearing surface replacement. However, corresponding embodiments are utilized for replacement of any of the other knee bearing surfaces and menisci, such as the right knee medial meniscus, left knee lateral meniscus, and/or right knee lateral meniscus. In that regard, the size, shape, thickness, material properties, and/or other properties of the prosthetic device may be configured for each particular application.

Figure 3:
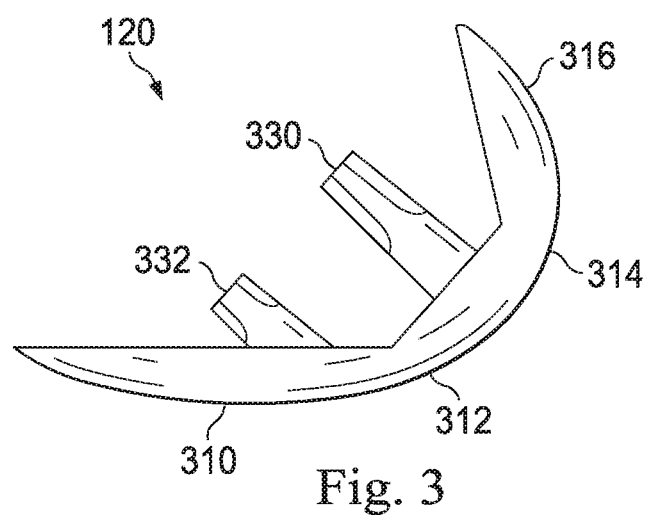
FIG. 3 is a side view of a femoral bearing component.
Figure 4:
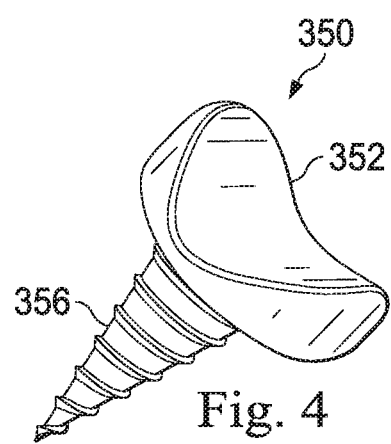
FIG. 4 is a diagrammatic perspective view of an alternative femoral bearing component.
Figure 5:
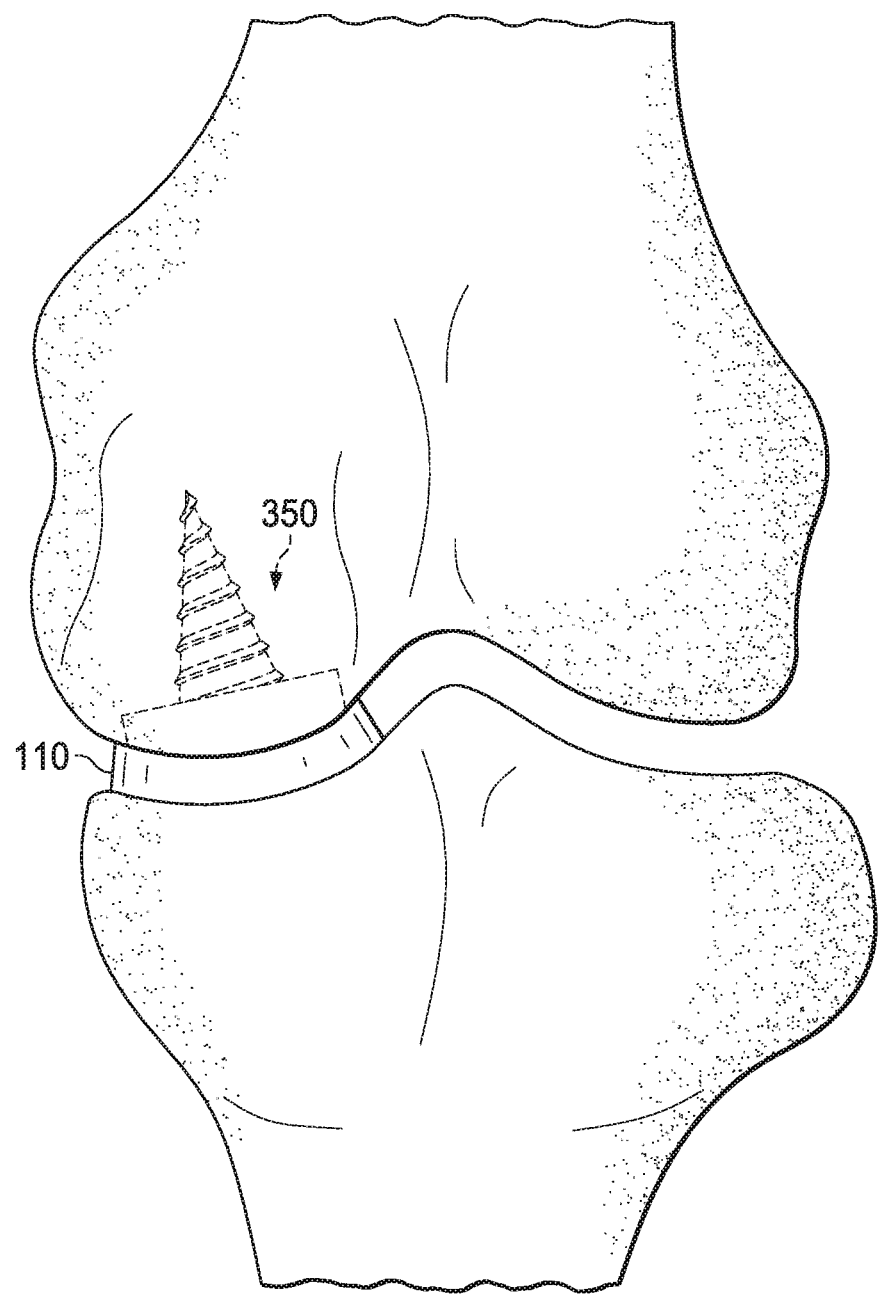
FIG. 5 is a front view of a partial unicompartmental knee replacement system according to one embodiment.

FIG. 3 illustrates a femoral bearing component 120. The femoral bearing component includes a first bearing area 310 having a first larger radius, a second bearing area 312 having a second radius smaller than the first, and a third bearing area 314 having a third radius smaller than the second radius, and a fourth bearing surface 316. Although a multi-radii femoral component is shown, it is possible that the femoral component can have a bearing surface with a single continuous bearing surface having a single radius or a number of radii less than or greater than the four shown in FIG. 3. In that regard, the one or radii of the femoral bearing component 120 can be selected to mimic the shape of a natural femur. The femoral bearing surface is held in place in the bone by insertion of the posts 330 and 332 into prepared bone holes. While two posts are shown, it will be appreciated that any number of anchoring extensions on the back side of the femoral component can be utilized to obtain a solid anchorage to the bone. The femoral component 120 replaces the patient femoral bearing surface on the side of the knee where it is used. For example, the femoral component 120 can be implanted to remedy a defect of either the medial condyle or the lateral condyle. An alternative femoral bearing component 350 is shown in FIG. 4. Femoral bearing component 350 has a smaller bearing surface that is intended to replace a relatively small defect in the natural femoral bearing surface such that surface 352 mimics the patient's bearing surface natural shape. As shown in FIG. 5, the femoral component 350 may be implanted into the knee using post 356 to retain its position along with a corresponding prosthetic meniscus device according to the present disclosure. The femoral component may be formed of any suitable biocompatible material, including but not limited to, cobalt chrome.

Figure 6:
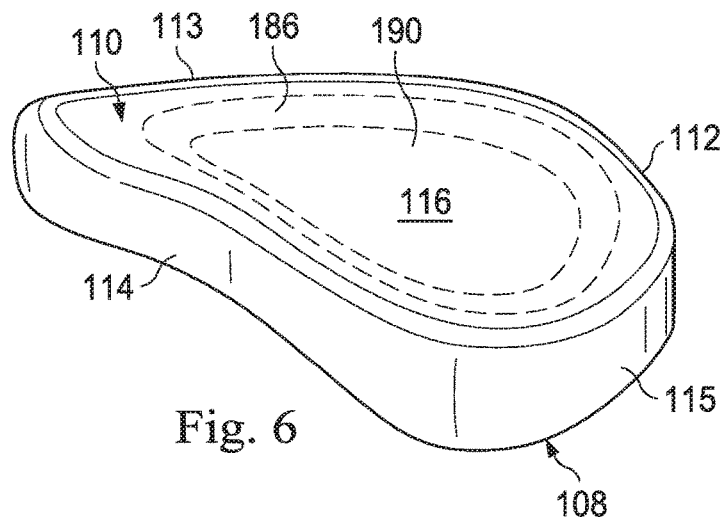
FIG. 6 is a perspective view of a prosthetic meniscus component.
Figure 7:
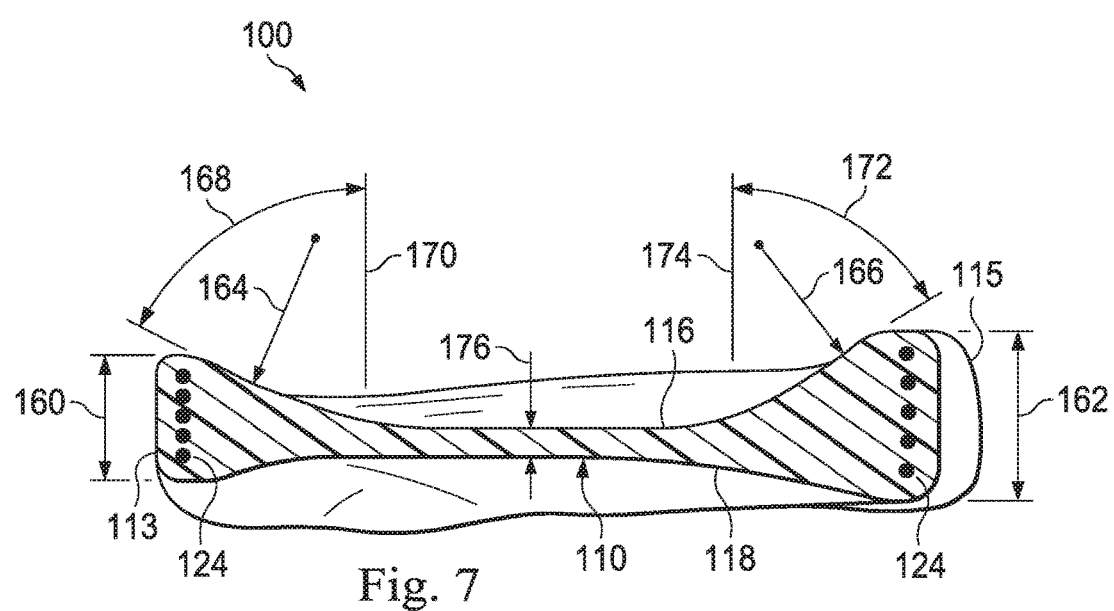
FIG. 7 is a cross section of the meniscus component of FIG. 6.

Referring now to FIGS. 6 and 7 shown therein is a prosthetic device having features similar to a prior design set forth in U.S. Pat. No. 8,361,147, which is hereby incorporated by reference in its entirety. Generally, the prosthetic device is for the replacement of the function a meniscus in a partial unicompartmental knee replacement system and is configured to interact with the replacement bearing surface to move the meniscus component to different engagement positions with opposing natural bearing surface. The prosthetic meniscus can be implanted to replace the lateral meniscus or the medial meniscus. In that regard, a prosthetic lateral meniscus is disposed between and in contact with an artificial lateral femoral bearing surface and the natural lateral tibial plateau. Similarly, a prosthetic medial meniscus is disposed between and in contact with an artificial medial femoral bearing surface and the natural medial tibial plateau. As described below, the prosthetic meniscus device can also be utilized with a natural femoral bearing surface and an artificial tibial bearing surface. The mobility of the meniscus device mimics a natural meniscus and distributes the loading stresses more naturally to the remaining natural bearing surface when utilized with a partial unicompartmental knee replacement system. The meniscus device is sized to interact with a specifically sized prosthetic femoral component. Thus, it is contemplated that the femoral component is matched to at least one meniscus device and that multiple matched pairs of implants will be available to treat patients with different knee anatomies and sizes.

The prosthetic meniscus comprises an outer body portion 108 and a central body portion 110. Generally, the outer body portion 108 has an increased thickness and height relative to the central body portion 110. In some instances the outer body portion 108 has a thickness between 5 mm and 15 mm. In some instances, the central body portion 110 has a thickness between 0.5 mm and 5 mm. In one particular embodiment, the outer body portion 108 has a maximum thickness of approximately 10 mm and the central body portion 110 has a maximum thickness of approximately 2 mm. The height or thickness of the outer body portion 108 varies around the perimeter of the prosthetic device in some instances. In that regard, the variations in the height or thickness of the outer body portion 108 are selected to match the anatomical features of the patient in some embodiments. Similarly, the height or thickness of the central body portion 110 varies across the prosthetic device in some embodiments. Again, the variations in the height or thickness of the central body portion 110 are selected to match the anatomical features of the patient in some embodiments. In some embodiments, the prosthetic device 100 is inserted in an insertion configuration and then loaded, stretched, moved, and/or otherwise transferred to an implantation configuration. In some embodiments the transformation between the insertion configuration and the implantation configuration is facilitated through the loading of the prosthetic device 100. In such embodiments, the variations in height or thickness of the outer and central body portions 108, 110 are selected to accommodate the deformation or transformation between the insertion configuration and the implantation configuration.

In the illustrated embodiment, the prosthetic device is configured for use without a fixation member or fixation device that would penetrate an adjacent bone and/or soft tissue to keep the prosthetic device in place. Rather, the prosthetic device 100 is configured to "float" within the knee joint without being secured by such bone and/or soft tissue-penetrating fixation devices or otherwise rigidly fixed to the femur, artificial femoral bearing component, artificial tibial bearing component or tibia and/or surrounding soft tissue. To that end, the outer body portion 108 of the prosthetic device 100 is shaped and sized to prevent unwanted expulsion of the prosthetic device from the knee joint. While bone must be removed to implant a femoral or tibial bearing component, the meniscus prosthetic device is implanted into a patient without causing permanent damage to the patient's undamaged tibia or other bone and/or soft tissue structure(s) engaged by the prosthetic device in some embodiments. In some instances the prosthetic device 100 is implanted to alleviate the patient's knee problems while avoiding permanent destruction of the patient's anatomy, such as cutting or reaming a large opening in the tibia. In such instances, the prosthetic device 100 may be subsequently removed and replaced with another prosthetic device or treatment without adversely affecting the subsequent treatment. In other instances where the femoral bearing surface remains intact, a tibial bearing component may be implanted before placement of the prosthetic meniscus device.

To this end, the outer body portion 108 of the prosthetic device includes a first portion 112 and a second portion or bridge 114. In some embodiments, the first portion 112 substantially matches the shape of a natural meniscus. In some embodiments, the outer body portion 108 has a semi-ellipsoidal shape. Accordingly, the first portion 112 extends around a majority of the outer body portion 108. The bridge 114 connects the two ends of the first portion 112. Thus, where the prosthetic device is configured for use as a medial meniscus device, the bridge 114 extends along the lateral side of the device. Where the prosthetic device is configured for use as a lateral meniscus device, the bridge 114 extends along the medial side of the device. Accordingly, the outer body portion 108—comprised of the first portion 112 and the bridge 114 and having an increased thickness relative to the central body portion 110—completely surrounds the central body portion 110 and serves to limit movement of the prosthetic device after implantation. That is, the increased height of the outer body portion 108 along with the contact pressure on the prosthetic device from being positioned between the femoral component and the tibia prevents the prosthetic device from moving outside of the desired range of positions within the knee joint.

The height or thickness of the bridge component 114 is based on the size of the femur notch and the distance to the cruciate ligaments in some embodiments. In some embodiments, the bridge 114 has a maximum height or thickness that is between ¼ and ¾ the maximum height or thickness of the first portion 112 of the outer body portion 108. In some embodiments, the size and shape of the bridge 114 is selected to achieve an optimal pressure distribution on the tibial plateau in order to mimic the pressure distribution of a healthy natural meniscus. The bridge 114 and, more generally, the outer body portion 108 are geometrically characterized by anterior, posterior, lateral-anterior, mid-lateral and lateral-posterior angles and heights as well as sagittal and coronal radii of curvature. Further, the outer body portion 108 and the central body portion 110 are shaped and sized such that the prosthetic device 100 is self-centering. That is, the shape and size of the prosthetic meniscus device itself encourages the prosthetic device to position or align itself with a desired orientation within the knee joint based on the position of the prosthetic femoral bearing component. Accordingly, as the prosthetic meniscus device moves through a range of positions within the knee joint it naturally returns to the desired orientation due to the shape and size of the outer and central body portion 108, 110. In some embodiments, the outer body portion and, more specifically, the bridge 114 acts as a physical barrier limiting the movement of the prosthetic device caused by joint reaction forces. The shape of the related femoral or tibial bearing component interacting with the self-centering or self-aligning mechanism combined with the prosthetic device's ability to move within the knee joint results in improved location of the prosthetic device 110 during typical gait cycles (e.g., flexion-extension angles of 0° to 20° or "heel-strike" to "toe-off"). The result is that the prosthetic device 110 exhibits a load pressure distribution similar to that of a natural meniscus.

The central body portion 110 defines an upper surface 116 and a lower surface 118. The upper and lower surfaces 116, 118 are both loaded surfaces. In particular, the upper and lower surfaces 116, 118 are configured to movingly engage with a prosthetic femoral bearing surface and a natural tibial plateau, respectively, or the inverse of a natural femoral bearing surface and an artificial tibial plateau, respectively. In that regard, the prosthetic device 110 can translate and rotate with respect to the femur and/or tibia within a range. In some instances, translation is possible in both the anterior-posterior and medial-lateral directions. In some embodiments, the upper surface 116 includes both a vertical and horizontal surface. To that end, in some embodiments the upper surface 116 comprises a concave surface that defines the vertical and horizontal surfaces. The thickness of the central body portion 110 between the upper surface 116 and the lower surface 118 supports stress distribution capability of the component, while the increased height of the upper surface 116 as it extends outwardly towards the outer body portion 108 defines the horizontal surface of the component. Similarly, in some embodiments the lower surface 118 includes both vertical and horizontal components. In particular, in some embodiments the lower surface 118 comprises a convex surface. The thickness of the central body portion 110 between the upper surface 116 and the lower surface 118 determines the load distribution capacity of the component, while the tapered height of the lower surface 116 as it extends outwardly towards the outer body portion 108 defines the horizontal component. In some embodiments, the upper surface 116 and/or the lower surface 118 are shaped such that the prosthetic device 100 is biased towards a neutral position in the knee. For example, the arcuate profiles of the upper surface 116 and/or the lower surface 118 are shaped such that the interaction between the surfaces and the prosthetic femoral component encourages the implant to a particular orientation relative to the surfaces. This allows the prosthetic device 100 to be self-centering or self-aligning as discussed further below.

Referring to FIG. 7, shown therein is a diagrammatic cross-sectional view of the prosthetic device 110 taken along an anterior to posterior section line between anterior end 113 and posterior end 115. The central body 110 is reinforced by pre-tensioned fibers 124 wound around the core to inhibit outward deformation while allowing inward flexibility. As shown, the anterior portion 113 of the outer body portion 108 has an anterior height or thickness 160. In that regard, the anterior height or thickness 160 of the anterior end 113 is between about 4 mm and immediately adjacent bridge structure 114 could be as great as about 15 mm and, in some instances, is between about 5.7 mm and about 9.3 mm. In the present embodiment, the anterior height or thickness 160 of the anterior end 113 is approximately 7.8 mm. In a smaller embodiment, the anterior height or thickness 160 is approximately 5.7 mm. In a larger embodiment, the anterior height or thickness 160 is approximately 9.3 mm. The posterior height or thickness 162 of the posterior end 114 is between about 4 mm and immediately adjacent the bridge structure 114 could be as great as about 20 mm and, in some instances, is between about 7.7 mm and about 12.7 mm. In the present embodiment, the posterior height or thickness 162 of the posterior end 115 is approximately 9.0 mm. In a smaller embodiment, the posterior height or thickness 162 is approximately 7.7 mm. In a larger embodiment, the posterior height or thickness 162 is approximately 12.7 mm.

The anterior portion of the upper surface of the anterior portion 113 has an anterior radius of curvature 164. In that regard, the anterior radius of curvature 164 is between about 10 mm and about 100 mm and, in some instances, is between about 23.0 mm and about 33.1 mm. In the present embodiment, the radius of curvature 164 is approximately 72 mm. In another embodiment, the radius of curvature 164 is approximately 28 mm. In a smaller embodiment, the radius of curvature 164 is approximately 23 mm. In a larger embodiment, the radius of curvature 164 is approximately 33.1 mm. The posterior portion of the upper surface of the posterior portion 115 has a posterior radius of curvature 166. In that regard, the posterior radius of curvature 166 is between about 5 mm and about 70 mm and, in some instances, is between about 15.2 mm and about 24.2 mm. In the present embodiment, the radius of curvature 166 is approximately 30 mm. In a smaller embodiment, the radius of curvature 166 is approximately 15.2 mm. In a larger embodiment, the radius of curvature 166 is approximately 24.2 mm.

Further, the anterior portion 113 of the upper surface generally extends at an anterior angle 168 with respect to an axis 170 extending substantially perpendicular to a plane generally defined by the prosthetic device 100, as shown. The anterior angle 168 is between about 45 degrees and about 75 degrees and, in some instances, is between about 62 degrees and about 68 degrees. In the present embodiment, the angle 168 is approximately 65 degrees. In a smaller embodiment, the angle 168 is approximately 62 degrees. In a larger embodiment, the angle is approximately 68 degrees. The posterior portion 115 of the upper surface generally extends at an posterior angle 172 with respect to an axis 174 extending substantially perpendicular to a plane generally defined by the prosthetic device 100, as shown. The posterior angle 172 is between about 35 degrees and about 70 degrees and, in some instances, is between about 55 degrees and about 61 degrees. In the present embodiment, the angle 172 is approximately 58 degrees. In a smaller embodiment, the angle 172 is approximately 50 degrees. In a larger embodiment, the angle 172 is approximately 65 degrees.

The central body portion 110 has a height or thickness 176 between the upper articulation surface 116 and the lower articulation surface 118. In some embodiments, the height or thickness 176 is the minimal thickness of the central body portion 110 and, in more specific embodiments, the minimal thickness of the entire prosthetic device 100. To that end, the height or thickness 176 is between about 1 mm and about 3 mm and, in some instances, is between about 1.2 mm and about 2.1 mm. In the present embodiment, the height or thickness 176 is approximately 1.5 mm. In a smaller embodiment, the height or thickness 176 is approximately 1.2 mm. In a larger embodiment, the height or thickness 176 is approximately 2.1 mm.

A variety of materials are suitable for use in making the prosthetic devices of the present disclosure. Medical grade polyurethane based materials especially suitable for use in the embodiments described include, but are not limited to, isolated or in combination, the following:

Bionate®, manufactured by DSM, a polycarbonate-urethane is among the most extensively tested biomaterials ever developed. Carbonate linkages adjacent to hydrocarbon groups give this family of materials oxidative stability, making these polymers attractive in applications where oxidation is a potential mode of degradation, such as in pacemaker leads, ventricular assist devices, catheters, stents, and many other biomedical devices. Polycarbonate urethanes were the first biomedical polyurethanes promoted for their biostability. Bionate® polycarbonate-urethane is a thermoplastic elastomer formed as the reaction product of a hydroxyl terminated polycarbonate, an aromatic diisocyanate, and a low molecular weight glycol used as a chain extender. The results of extensive testing encompassing Histology, Carcinogenicity, Biostability, and Tripartite Biocompatibility Guidance for Medical Devices verifies the cost effective material's biocompatibility.

Another group of suitable materials are copolymers of silicone with polyurethanes as exemplified by PurSil™, a Silicone Polyether Urethane and CarboSil™, a Silicone Polycarbonate Urethane. Silicones have long been known to be biostable and biocompatible in most implants, and also frequently have the low hardness and low modulus useful for many device applications. Conventional silicone elastomers can have very high ultimate elongations, but only low to moderate tensile strengths. Consequently, the toughness of most biomedical silicone elastomers is not particularly high. Another disadvantage of conventional silicone elastomers in device manufacturing is the need for cross-linking to develop useful properties. Once cross-linked, the resulting thermoset silicone cannot be redissolved or remelted. In contrast, conventional polyurethane elastomers are generally thermoplastic with excellent physical properties. Thermoplastic urethane elastomers (TPUs) combine high elongation and high tensile strength to form tough, albeit fairly high-modulus elastomers. Aromatic polyether TPUs can have an excellent flex life, tensile strength exceeding 5000 psi, and ultimate elongations greater than 700 percent. These materials are often used for continuously flexing, chronic implants such as ventricular-assist devices, intraaortic balloons, and artificial heart components. TPUs can easily be processed by melting or dissolving the polymer to fabricate it into useful shapes.

The prospect of combining the biocompatibility and biostability of conventional silicone elastomers with the processability and toughness of TPUs is an attractive approach to what would appear to be a nearly ideal biomaterial. For instance, in polycarbonate-based polyurethanes, silicone copolymerization has been shown to reduce hydrolytic degradation of the carbonate linkage, whereas in polyether urethanes, the covalently bonded silicone seems to protect the polyether soft segment from oxidative degradation in vivo. DSM synthesized silicone-polyurethane copolymers by combining two previously reported methods: copolymerization of silicone (PSX) together with organic (non-silicone) soft segments into the polymer backbone, and the use of surface-modifying end groups to terminate the copolymer chains.

Other applicable materials include PurSil™ silicone-polyether-urethane and CarboSil™ silicone-polycarbonate-urethane which are true thermoplastic copolymers containing silicone in the soft segment. These high-strength thermoplastic elastomers are prepared through a multi-step bulk synthesis where polydimethylsiloxane (PSX) is incorporated into the polymer soft segment with polytetramethyleneoxide (PTMO) (PurSil) or an aliphatic, hydroxyl-terminated polycarbonate (CarboSil). The hard segment consists of an aromatic diisocyanate, MDI, with low molecular weight glycol chain extender. The copolymer chains are then terminated with silicone (or other) Surface-Modifying End Groups. Aliphatic (AL) versions of these materials, with a hard segment synthesized from an aliphatic diisocyanate, are also available.

Many of these silicone urethanes demonstrate desirable combinations of physical properties. For example, aromatic silicone polyetherurethanes have a higher modulus at a given shore hardness than conventional polyether urethanes—the higher the silicone content, the higher the modulus (see PurSil Properties). Conversely, the aliphatic silicone polyetherurethanes have a very low modulus and a high ultimate elongation typical of silicone homopolymers or even natural rubber (see PurSil AL Properties). These properties make these materials very attractive as high-performance substitutes for conventional cross-linked silicone rubber. In both the PTMO and PC families, some polymers have tensile strengths three to five times higher than conventional silicone biomaterials.

Further examples of suitable materials include Surface Modifying End Groups (SMEs) which are surface-active oligomers covalently bonded to the base polymer during synthesis. SMEs—which include silicone (S), sulfonate (SO), fluorocarbon (F), polyethylene oxide (P), and hydrocarbon (H) groups—control surface chemistry without compromising the bulk properties of the polymer. The result is that key surface properties, such as thromboresistance, biostability, and abrasion resistance, are permanently enhanced without additional post-fabrication treatments or topical coatings. This technology is applied to a wide range of DSM's polymers.

SMEs provide a series of base polymers that can achieve a desired surface chemistry without the use of additives. Polyurethanes prepared according to DSM's development process couple endgroups to the backbone polymer during synthesis via a terminal isocyanate group, not a hard segment. The added mobility of endgroups relative to the backbone facilitates the formation of uniform overlayers by the surface-active end blocks. The use of the surface active endgroups leaves the original polymer backbone intact so the polymer retains strength and processability. The fact that essentially all polymer chains carry the surface-modifying moiety eliminates many of the potential problems associated with additives.

The SME approach also allows the incorporation of mixed endgroups into a single polymer. For example, the combination of hydrophobic and hydrophilic endgroups gives the polymers amphipathic characteristics in which the hydrophobic versus hydrophilic balance may be easily controlled.

Other suitable materials, manufactured by CARDIOTECH CTE, include ChronoFlex® and Hydrothane™.

The ChronoFlex®, polycarbonate aromatic polyurethanes, family of medical-grade segmented biodurable polyurethane elastomers have been specifically developed by CardioTech International to overcome the in vivo formation of stress-induced microfissures.

HydroThane™, hydrophilic thermoplastic polyurethanes, is a family of super-absorbent, thermoplastic, polyurethane hydrogels ranging in water content from 5 to 25% by weight. HydroThane™ is offered as a clear resin in durometer hardness of 80A and 93 Shore A. The outstanding characteristic of this family of materials is the ability to rapidly absorb water, high tensile strength, and high elongation. The result is a polymer having some lubricious characteristics, as well as being inherently bacterial resistant due to their exceptionally high water content at the surface. HydroThane™ hydrophilic polyurethane resins are thermoplastic hydrogels, and can be extruded or molded by conventional means. Traditional hydrogels on the other hand are thermosets and difficult to process.

Additional suitable materials manufactured by THERMEDICS include Tecothane® (aromatic polyether-based polyurethane), Carbothane® (aliphatic polycarbonate-based polyurethane), Tecophilic® (high moisture absorption aliphatic polyether-based polyurethane) and Tecoplast® (aromatic polyether-based polyurethane). Tecothane® is a family of aromatic, polyether-based TPU's available over a wide range of durometers, colors, and radiopacifiers. One can expect Tecothane resins to exhibit improved solvent resistance and biostability when compared with Tecoflex resins of equal durometers. Carbothane® is a family of aliphatic, polycarbonate-based TPU's available over a wide range of durometers, colors and radiopacifiers. This type of TPU has been reported to exhibit excellent oxidative stability, a property which may equate to excellent long-term biostability. This family, like Tecoflex, is easy to process and does not yellow upon aging. Tecophilic® is a family of aliphatic, polyether-based TPU's which have been specially formulated to absorb equilibrium water contents of up to 150% of the weight of dry resin.

Additional materials of interest include Tecogel, a new member to the Tecophilic family, a hydrogel that can be formulated to absorb equilibrium water contents between 500% to 2000% of the weight of dry resin, and Tecoplast®, a family of aromatic, polyether-based TPU's formulated to produce rugged injection molded components exhibiting high durometers and heat deflection temperatures.

Additional potentially suitable materials include four families of polyurethanes, named Elast-Eon™, which are available from AorTech Biomaterials.

Elast-Eon™ 1, a Polyhexamethylene oxide (PFMO), aromatic polyurethane, is an improvement on conventional polyurethane in that it has a reduced number of the susceptible chemical groups. Elast-Eon™ 2, a Siloxane based macrodiol, aromatic polyurethane, incorporates siloxane unto the soft segment. Elast-Eon™ 3, a Siloxane based macrodiol, modified hard segment, aromatic polyurethane, is a variation of Elast-Eon™ 2 with further enhanced flexibility due to incorporation of siloxane into the hard segment. Elast-Eon™ 4 is a modified aromatic hard segment polyurethane.

Bayer Corporation also produces candidate materials. Texin 4210 and Texin 4215 are thermoplastic polyurethane/polycarbonate blends for injection molding and extrusion. Texin 5250, 5286 and 5290 are aromatic polyether-based medical grade materials with Shore D hardness of approximately 50, 86, and 90 respectively for injection molding and extrusion.

In some embodiments, the prosthetic device is a melt mold composite implant composed of two biocompatible materials: DSM Bionate® Polycarbonate-Urethane (PCU), 80 Shore A, matrix material and ultra high molecular weight polyethylene (UHMWPE) reinforcement material (Dyneema Purity). In some particular embodiments, a prosthetic device formed of PCU and reinforced circumferentially with DSM Dyneema® fibers results in a desirable distribution of loads on the underlying articulation surfaces of the prosthetic device.

Figure 8:
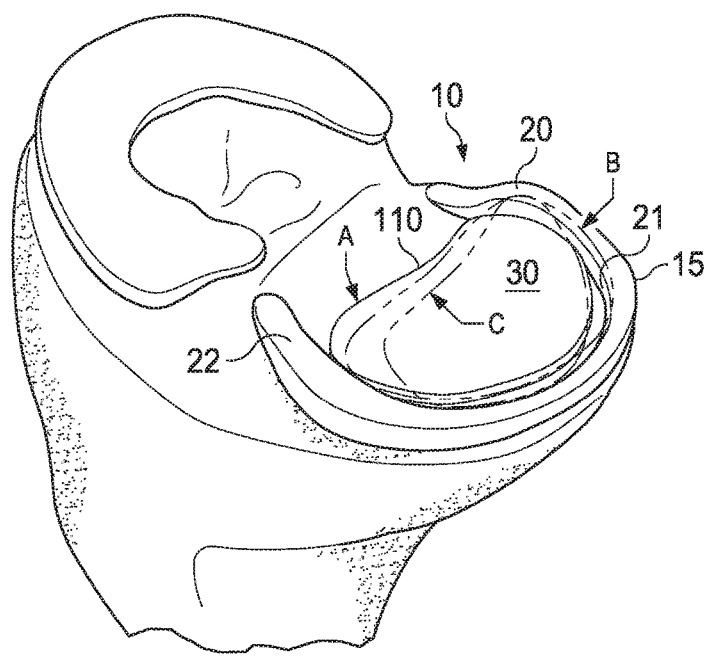
FIG. 8 is a perspective view of a knee illustrating an implanted meniscus device in a series of positions.

Referring now to FIG. 8, there is shown a top view of a knee joint with an injured meniscus 10. The meniscus includes an outer rim 15 that is anchored to the bone along the posterior rim 20 and the anterior rim 22. Referring to FIG. 8, the torn segments along with the undamaged central meniscus have been removed to expose the underlying tibia and define an implantation area 30. The implantation area 30 is bounded by sidewall 21. A prosthetic meniscus device 110 according to one aspect of the current disclosure is positioned in the meniscus pocket 30 defined by the sidewall 21. As will be explained in greater detail below, the prosthetic meniscus engages an artificial femoral bearing component to move the meniscus device into positions A, B and C within the meniscus pocket 30. In that regard, the positions A, B, and C can be longitudinally, rotationally, and/or laterally offset from one another.

Figure 9A:
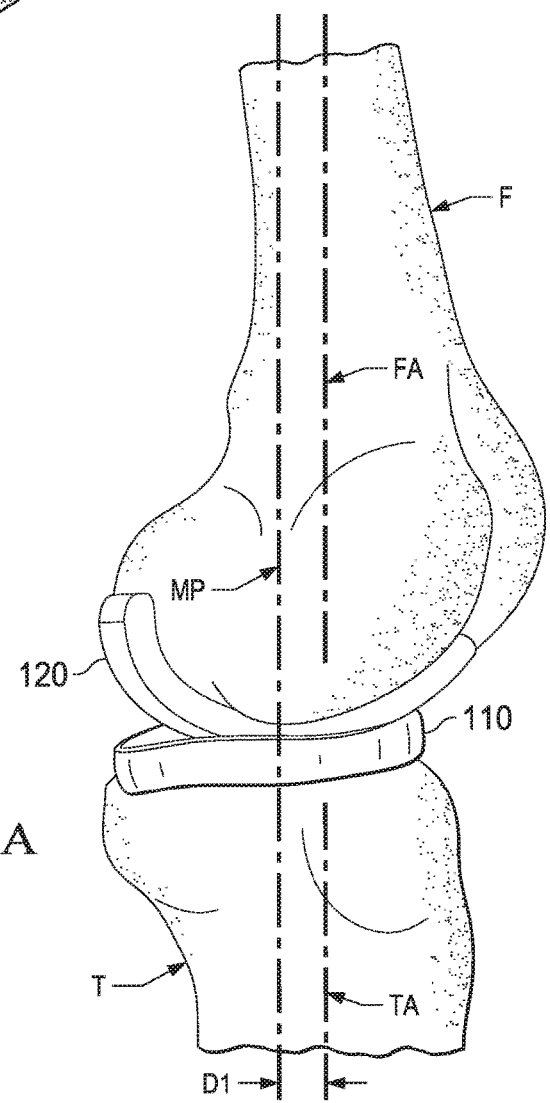
FIGS. 9A-9C illustrate an implanted partial unicompartmental knee replacement system according to the present invention with the knee articulated through a series of angles.
Figure 9B:
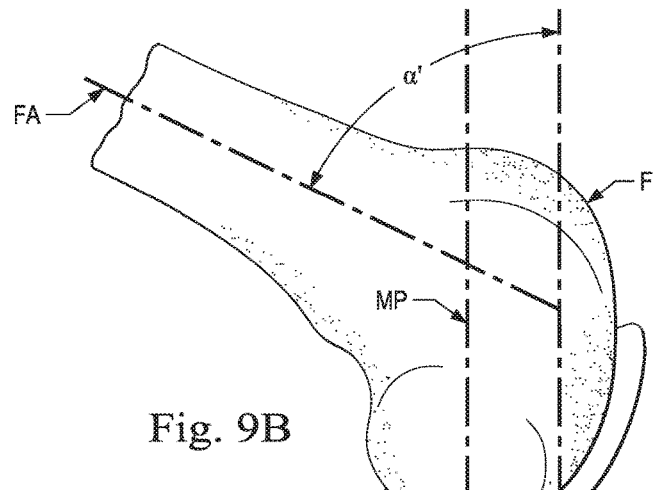
Figure 9B:
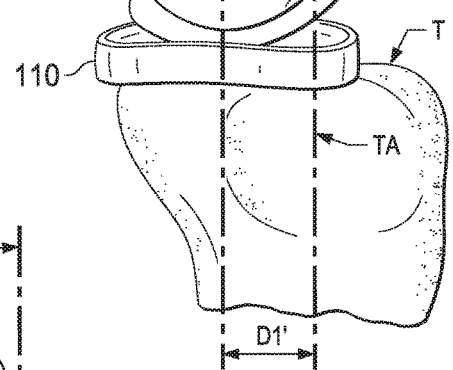
Figure 9C:
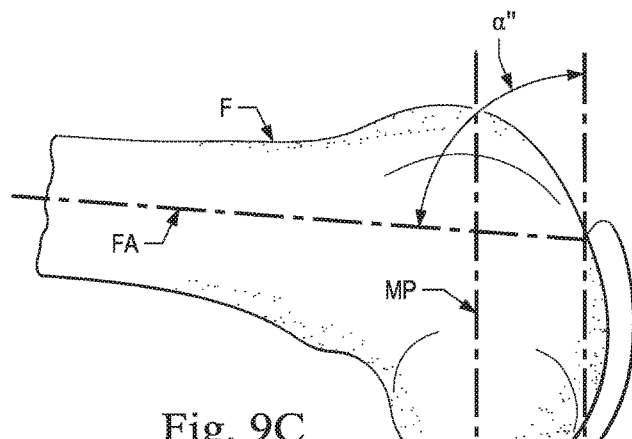
Figure 9C:
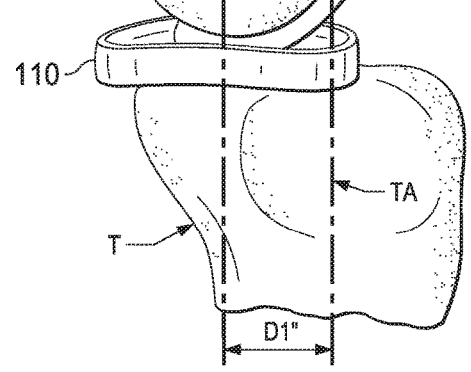
Figure 10A:
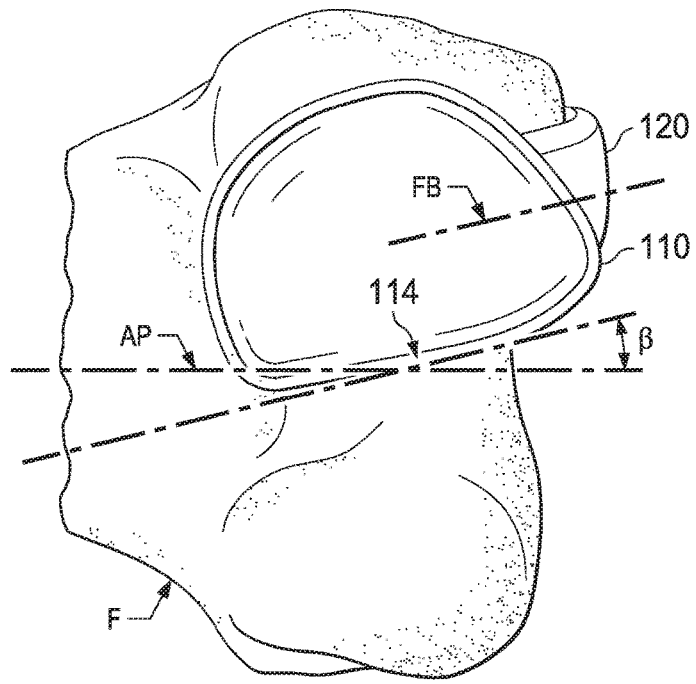
FIGS. 10A-10C illustrate the rotational position of the meniscus component of the system in FIGS. 9A-9C.

Referring now to FIGS. 9A-9C, there is shown an artificial femoral bearing component (FBC) 120 implanted on a femur F and a prosthetic meniscus device (PMD) 110 positioned between the femoral bearing component and the natural tibial plateau of the tibia T. With the axis of the femur FA aligned with the axis of the tibia TA, a first bearing portion of the FBC engages the PMD and the PMD is positioned in a first position A with respect to the tibia. The position of the PMD 110 can be characterized by a superior-inferior axis MP extending through the midpoint of the PMD. In position A, the PMD is offset from the tibial axis TA by distance D1. Distance D1 describes the separation between the axis MP of the PMD and the tibial axis TA. FIG. 10A illustrates the view from the tibia in position A and shows the rotational orientation of the PMD sidewall 114 in relation to the anterior-posterior axis AP, as well as the orientation of the PMD 110 to the axis FB extending from the anterior to the posterior of the FBC 120. In position A, the angle between the edge of the PMD 120 and the axis AP is β.

Figure 10B:
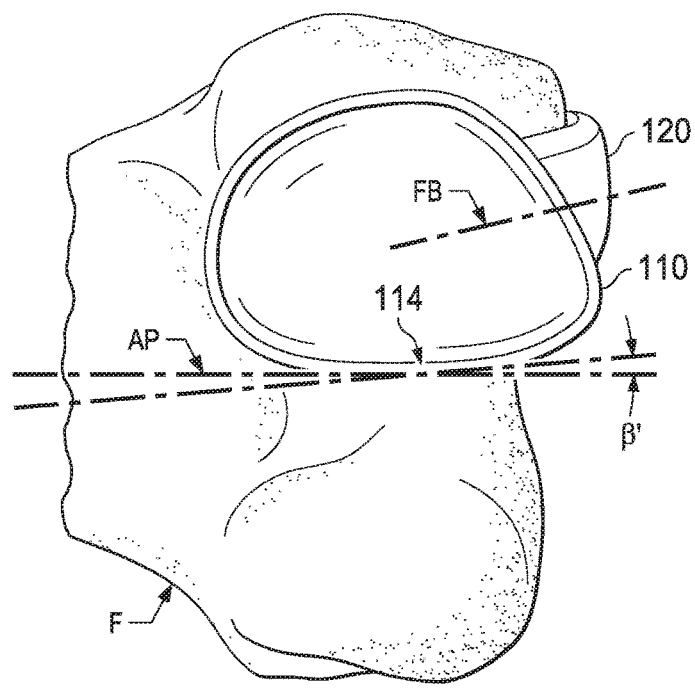

Referring now to FIGS. 9B and 10B, these figures illustrate the movement of the PMD as the femur F is moved to the position of the angle α' between axis FA and axis TA. The PMD is now engaged with a second bearing surface of the FBC having a different radius of curvature. As a result of this contact, the PMD 110 has translated posteriorly and is now spaced a distance D1' from the axis TA, which is greater than D1. Additionally, the PMD 110 has rotated clockwise with respect to axis AP to smaller angle β'. The illustrated relationship is position B. The PMD 110 has moved longitudinally, rotationally, and/or laterally between positions A and B. Translation of the PMD 110 along the axis AP can be described as longitudinal movement. Translation of the PMD 110 along a medial-lateral axis perpendicular to the axis AP can be described as lateral movement.

Figure 10C:
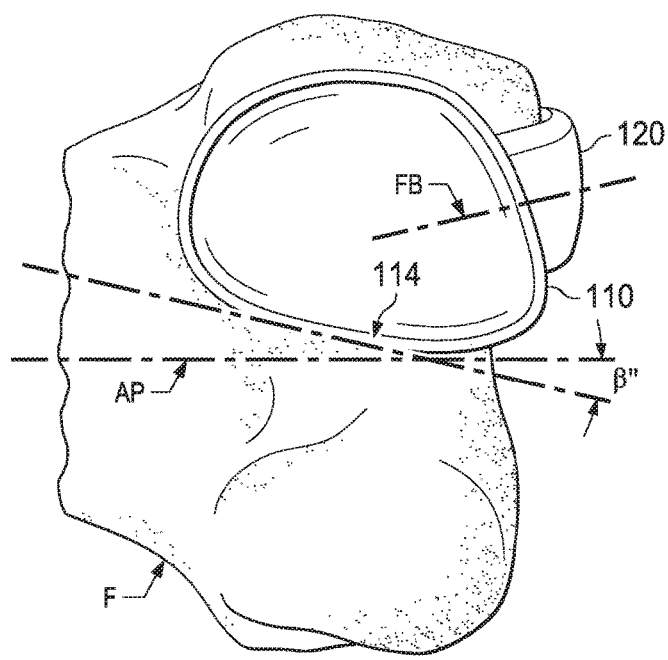

Referring now to FIGS. 9C and 10C, continued rotation of the femur with respect to the tibia results in angle α" which is greater than angle α' and almost 90 degrees. The PMD is now engaged with a third bearing surface of the FBC having a different radius of curvature. As a result of this contact, the PMD 110 has translated posteriorly and is now spaced a distance D1" from the axis TA, which is greater than D1'. Additionally, the PMD 110 has rotated clockwise with respect to axis AP to smaller angle β" which now a negative angle in comparison to the AP axis. The illustrated relationship is position C. The PMD 110 has moved longitudinally, rotationally, and/or laterally between positions B and C, and positions A and C.

While the foregoing are not limiting, the PMD total translation distance D1 can range from 3-20 mm in the anterior to posterior plane, with one embodiment having D1 of 5 mm, D1' of 10 mm and D1" of 15 mm. Similarly, the PMD rotational angle can range, without limitation, from 3 to 30 degrees of total angular rotation. With respect to the embodiment shown in FIGS. 10A-10C, β is approximately 10 degrees, β' is approximately 5 degrees, and β" is approximately −5 degrees from the AP line. Although the angles are shown with respect to the AP line, the sidewall 114 also varies by the same angular amounts from the axis FB of the FBC 120.

As shown above with respect to FIGS. 9A-10C, as the first, second and third regions of the FBC engage the PMD, the PMD is floating on the natural tibial plateau and translates while simultaneously rotating into the positions shown. In one form, the first bearing surface of the FBC engages a first meniscus bearing surface on the PMD to force the device 110 into position A, while a second bearing surface on the FBC engages a second meniscus bearing surface on the PMD to force the device into position B, while a third bearing surface on the FBC engages a third meniscus bearing surface on the PMD to force the device into position C.

Figure 11A:
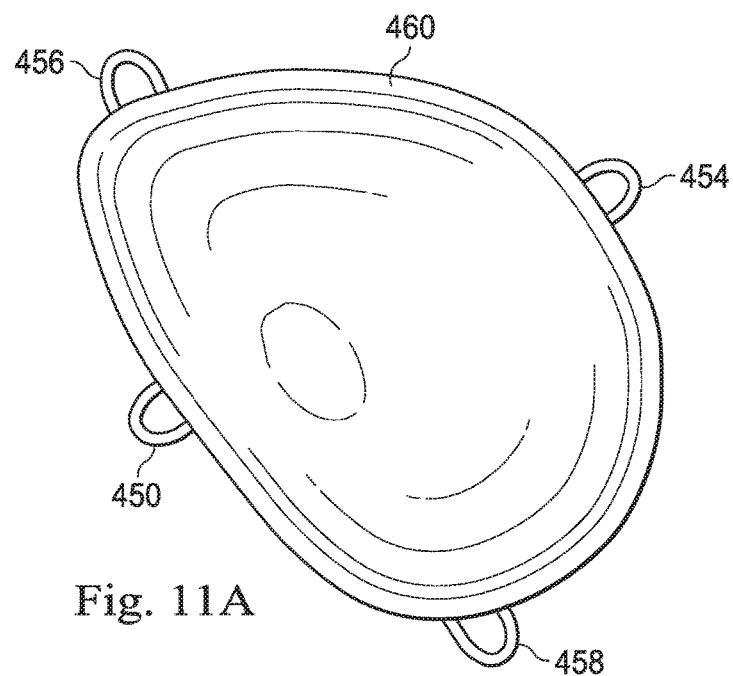
FIGS. 11A and 11B illustrate a meniscus device with tethering loops.
Figure 11B:
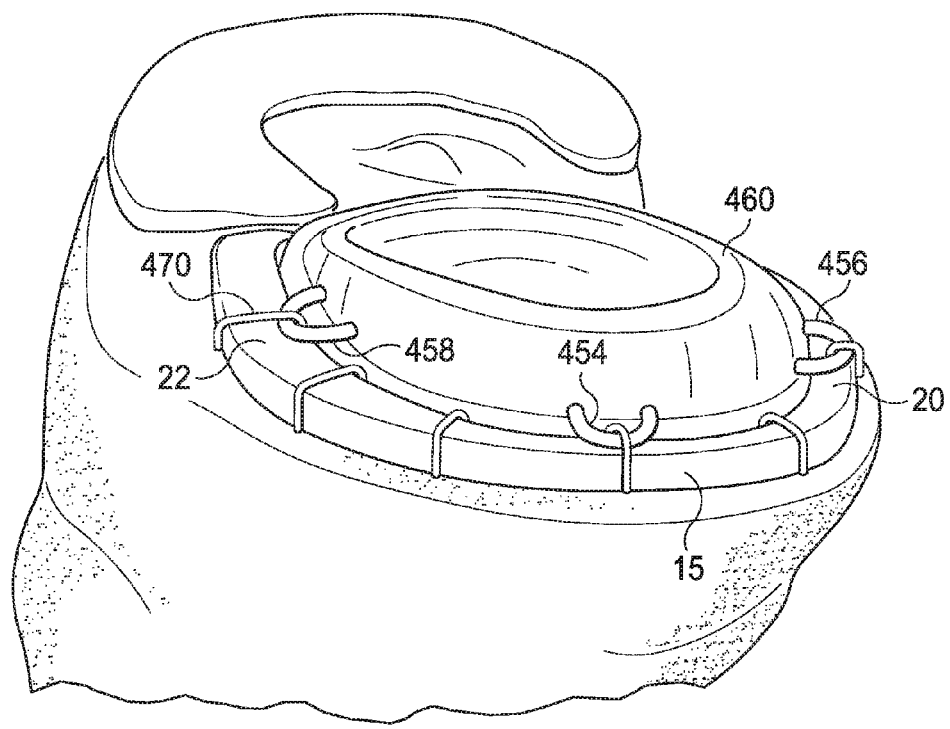
Figure 12A:
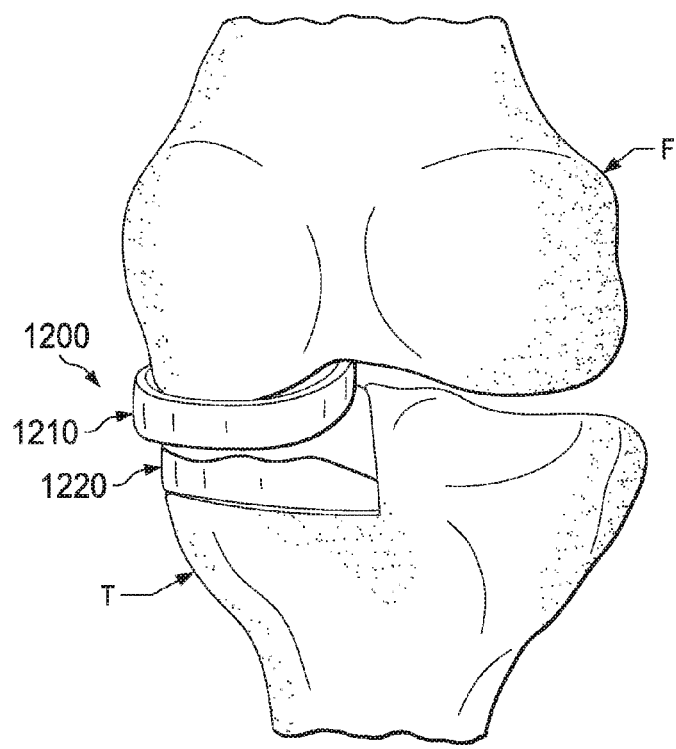
FIGS. 12A-12C are diagrammatic illustrations of a prosthetic partial unicompartmental knee replacement system of a further embodiment associated with the knee joint.
Figure 12B:
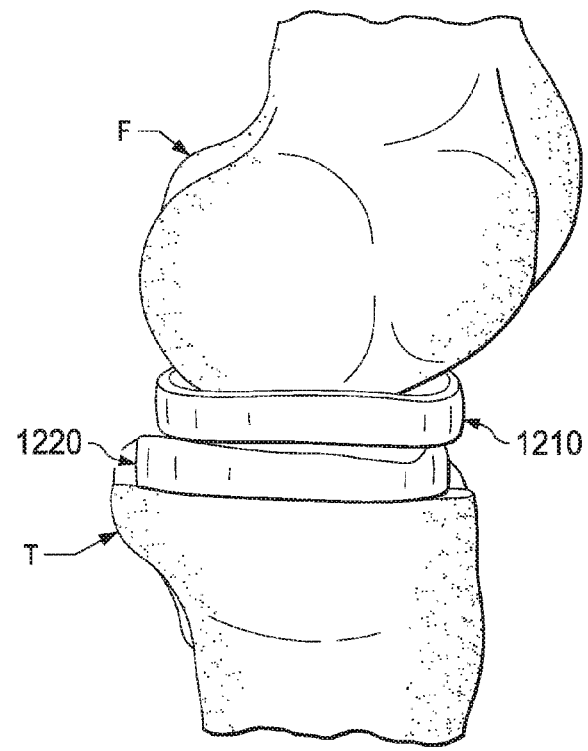
Figure 12C:
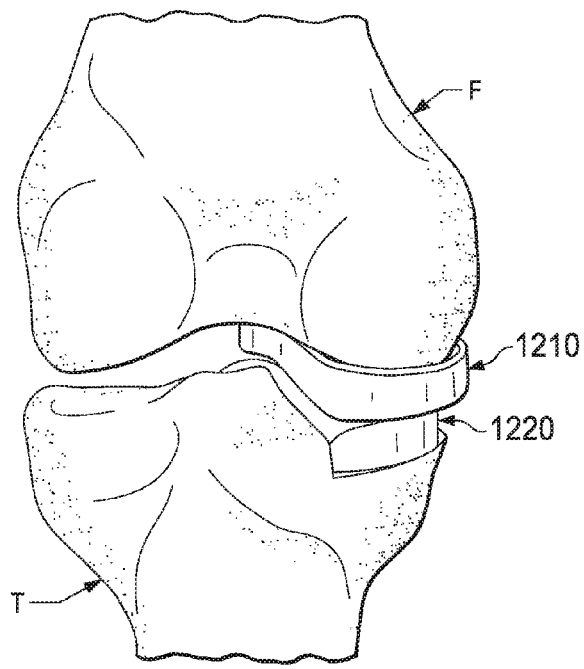
Figure 13A:
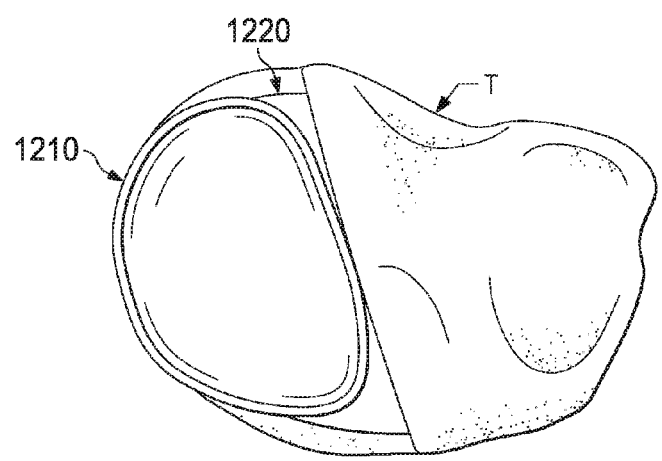
FIGS. 13A-13C illustrate various views of the system of FIG. 12A.
Figure 13B:
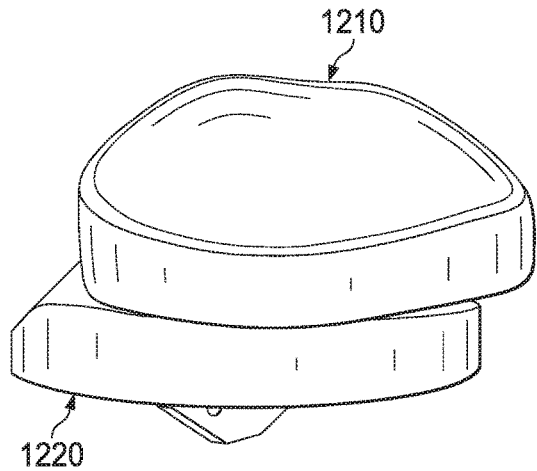
Figure 13C:
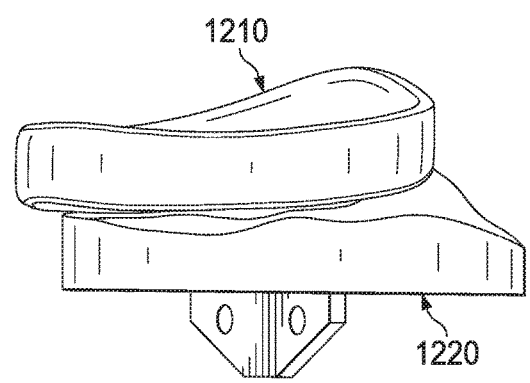
Figure 14A:
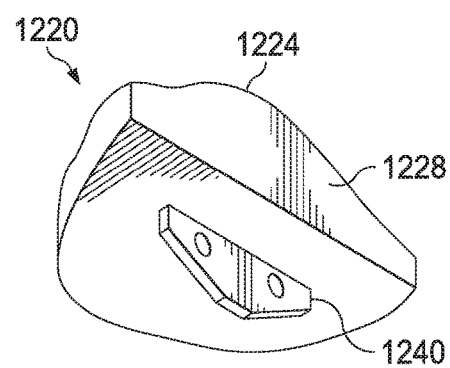
FIGS. 14A-15C illustrate various views of the tibial plateau bearing component associated with the system of FIG. 12A.
Figure 14B:
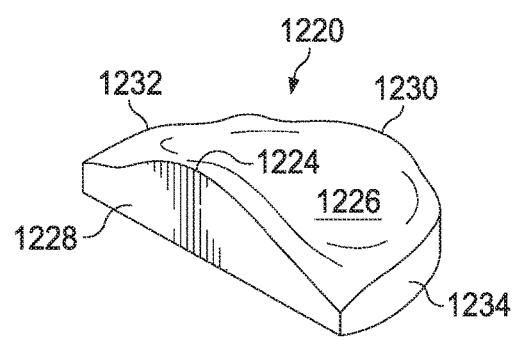
Figure 14C:
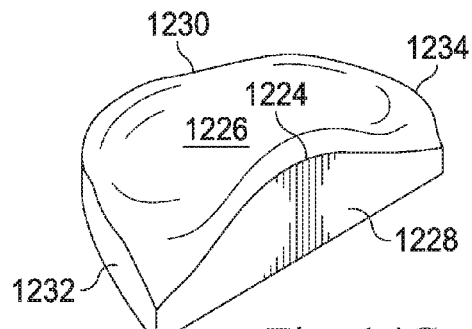
Figure 15A:
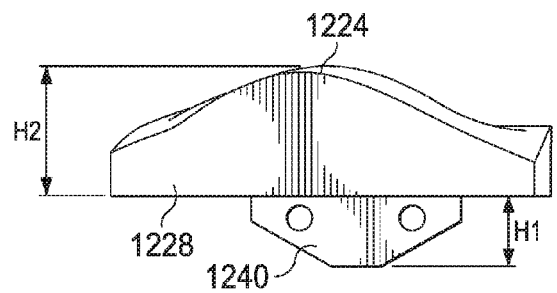
Figure 15B:
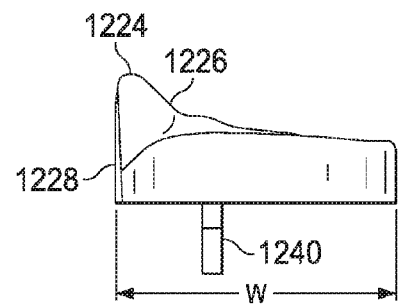
Figure 15C:
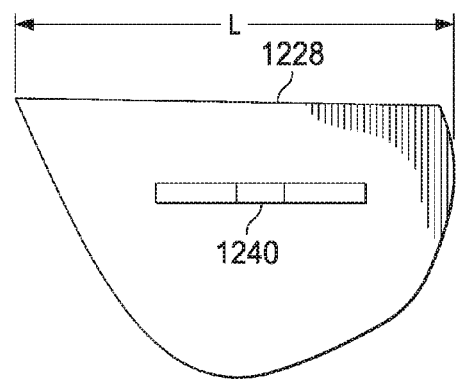

Referring now to FIGS. 11A and 11B, there is shown a further embodiment of a meniscus replacement device 460 according to another aspect of the present disclosure. The implant 460 includes tethering loops 450, 454, 456 and 458. As explained more fully in U.S. application Ser. No. 14/212, 330 filed Mar. 14, 2014 entitled "Meniscus Prosthetic Devices with Anti-Migration or Radiopaque Features", incorporated by reference herein in its entirety, the loops are formed by a series of fibers loosely wound around a core after the tension elements are positioned, with slack portions held outwardly during the over-flow molding process to form the loops. Thus, in one form, the loops 450, 454, 456 and 458 are formed of a series of filaments that are partially embedded within the over molded area and partially extending beyond the sidewalls. The loops themselves may also include a coating of the over molding material. In one form, each loop has a unique set of filaments extending around the core such that if one loop is cut off, severing of the fibers will not impact the remaining loops. In still a further form, one or more fiber reinforced tabs extend outwardly from the outer side wall. Although the tabs lack a preformed opening, the tabs provide fiber reinforced areas for the passage of a needle and suture that can firmly retain the suture without damaging the pliable material of the implant. In one aspect, the tabs are spaced around the implant at strategic locations, while in another form, the fiber reinforced tab extends completely around the side wall perimeter of the implant.

In use, the implant 460 can be inserted into the joint space after implantation of the femoral bearing component 120. In one aspect, the anterior tethering loop 458 is positioned adjacent the anterior rim 22 and a suture 470 is passed through the loop 458 and the anterior rim 22. The tension applied to the suture can be varied to provide the correct amount of freedom of movement within the joint space. The other tether loops that are not used can be severed by the physician before implantation in the joint space. In an alternative placement, the implant 460 is positioned in the spaced formed within the remaining portions of the meniscus 15 with the tethering loop 456 positioned adjacent the posterior rim 20. A suture is passed through the loop 456 and the posterior rim 20 to maintain the implant within the joint space. In both the described tethering arrangements, the implant 460 has a high degree of freedom of movement with the joint space such that the implant retains its ability to float freely within the joint to mimic a natural meniscus. In still a further aspect, the one or more tether loops 454, 456 and 458 are attached to the soft tissue of the joint capsule.

Referring now to FIG. 11B, the implant 460 is more fully tethered in the joint space by a suture that extends through all or part of the tether loops 454, 456 and 458 and around the meniscus rim 15 including the posterior rim 20 and the anterior rim 22. In this arrangement, the implant 460 is constrained to a more limited zone of movement providing a limited range of motion, although it is permitted to translate anterior to posterior, and to rotate with respect to the tibial plateau.

Referring now to FIGS. 12A-13C, there is shown a further form of a partial unicompartmental knee replacement system according to another aspect of the present disclosure. The PUKR 1200 includes a prosthetic meniscus device (PMD) 1210 and an artificial tibial bearing component 1220. In that regard, the PMD 1210 is disposed between and in contact with the artificial tibial bearing component 1220 and the natural femoral bearing surface. The upper surface of the PMD 1210 is shaped generally as described above with a meniscus bearing surface configured to engage a first, second and third bearing surface of the femur. As also described above, the first, second, and third bearing surfaces of the natural femur can have respective first, second, and third radii of curvature. The lower surface of the PMD 1210 is shaped to engage the TBC 1220 and move the PMD through a variety of positions as explained below.

As shown in FIGS. 14A-15C, the tibial bearing component includes a keel 1240, having a height H1, for positioning in a bone channel in the tibia to anchor the device in a stationary position with respect to the tibia. The TBC includes a medial side wall 1228 and a peak 1224 defining the maximum height H2. The TBC has a maximum width of W and length of L. In one embodiment, H1 is approximately 8 mm, H2 is approximately 14 mm, W is approximately 31 mm and L is approximately 49 mm. A bearing surface 1226 extends between sidewalls 1228 and 1230, and end walls 1232 and 1234. The bearing surface 1226 includes a convex region adjacent peak 1224.

Figure 16A:
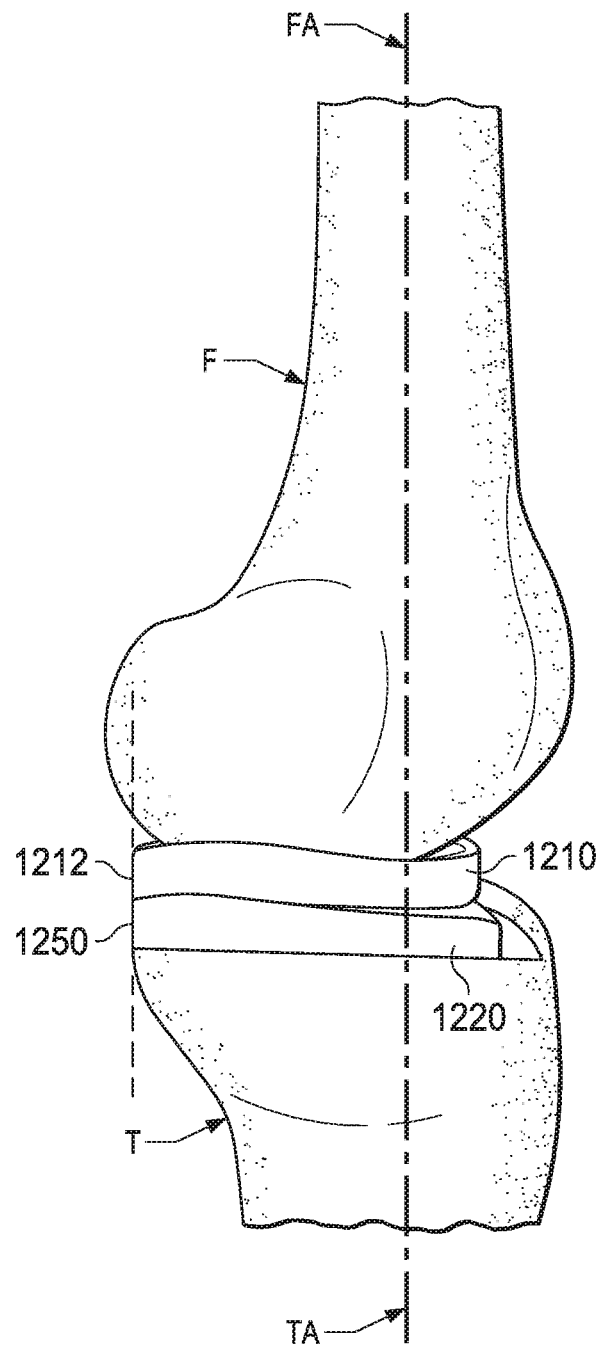
FIGS. 16A-16D illustrate an implanted partial unicompartmental knee replacement system according to FIG. 12A with the knee articulated through a series of angles.

Referring now to FIGS. 16A-17C, there is shown a series of angular positions of the femur in relation to the tibia and the corresponding movement of the PUKR system in the knee joint. In FIG. 16A, femoral axis FA is substantially aligned with the tibial axis TA. In this position, A, the posterior wall 1212 of the PMD 1210 is substantially aligned with the posterior wall 1250 of the TBC 1220. With the axis of the femur FA aligned with the axis of the tibia TA, a first bearing portion of the TBC engages the PMD and the PMD is positioned in a first position A with respect to the tibia. FIG. 17A illustrates the view from the femur in position A and shows the rotational orientation of the PMD in relation to the sidewall 1228 of the TBC shown by the line TP, as well as the orientation of the PMD to the tibia. The line TP represents an anterior-posterior axis along the sidewall 1228 of the TBC 1220. In position A, the angle between the medial edge of the PMD 1210 and the line TP is A.

Figure 16B:
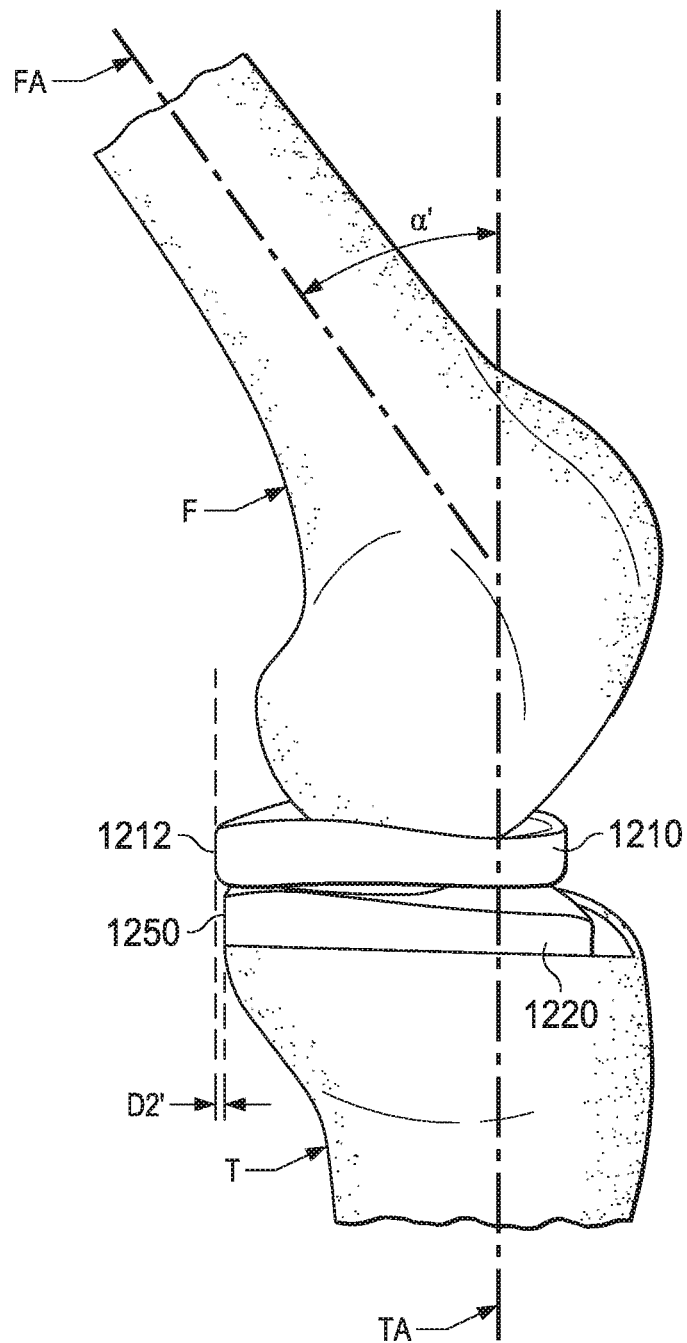
Figure 17A:
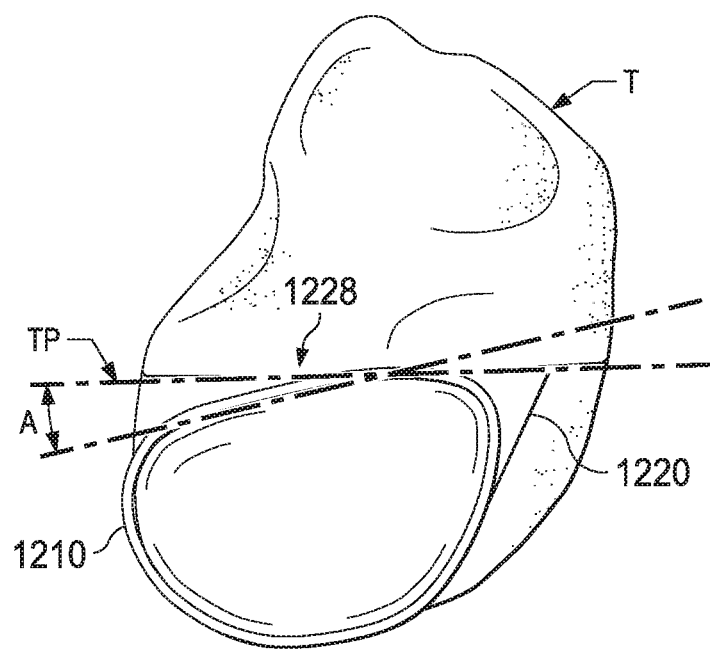
FIGS. 17A-17C illustrate the rotational position of the meniscus component of the system shown in FIGS. 16A-16D.
Figure 17B:
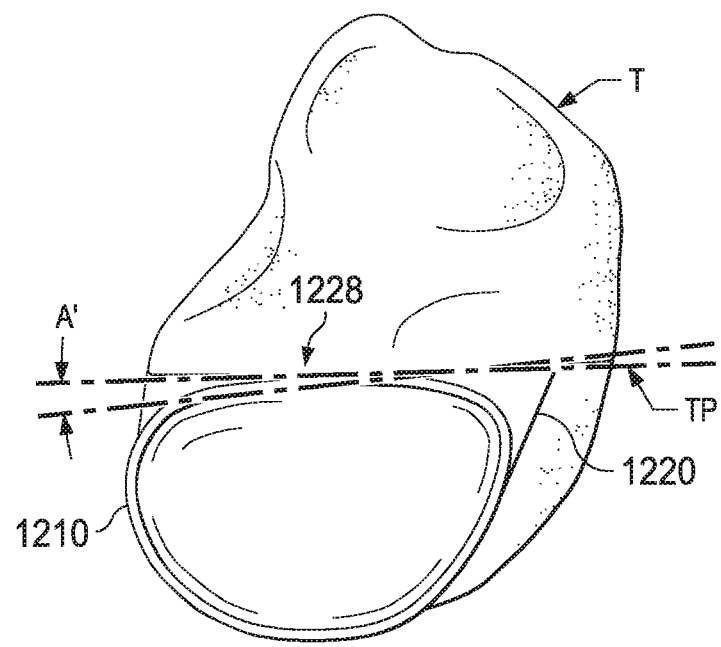

Referring now to FIGS. 16B and 17B, these figures illustrate the movement of the PMD 1210 as the femur F is moved to the position of the angle $\alpha'$ between axis FA and axis TA. The PMD 1210 is now engaged with a second bearing surface of the natural femur having a different radius of curvature causing the PMD to engage the TBC bearing surface 1226 resulting in translation and rotation of the PMD as shown in FIGS. 16B and 17B. As a result of this contact, the PMD 110 has translated posteriorly and now has its posterior wall 1212 spaced a distance D2' from the posterior wall 1250 of the TBC 1220. Additionally, the PMD 1210 has rotated clockwise with respect to line TP to smaller angle A'. The illustrated relationship is position B. The PMD 110 has moved longitudinally, rotationally, and/or laterally between positions A and B.

Figure 16C:
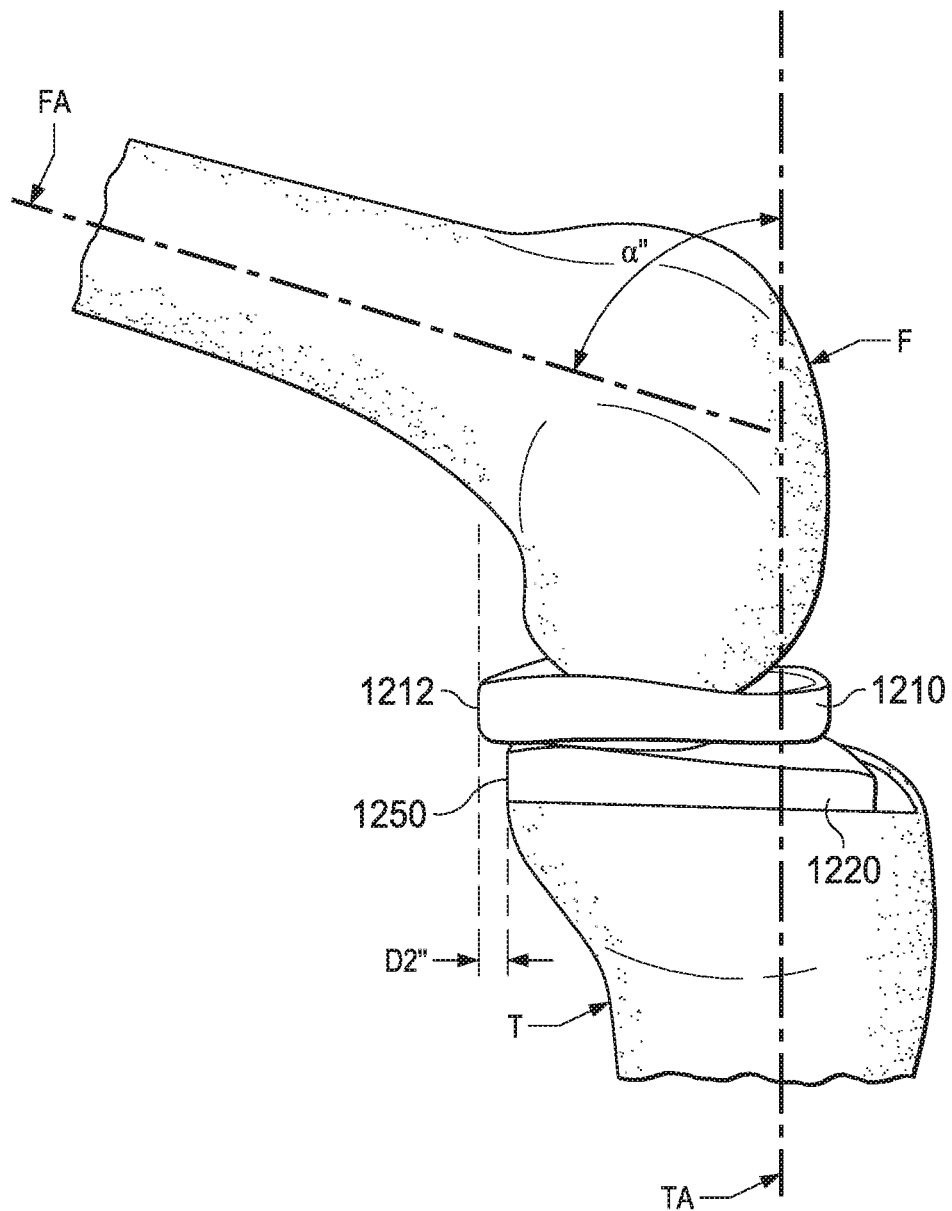
Figure 17C:
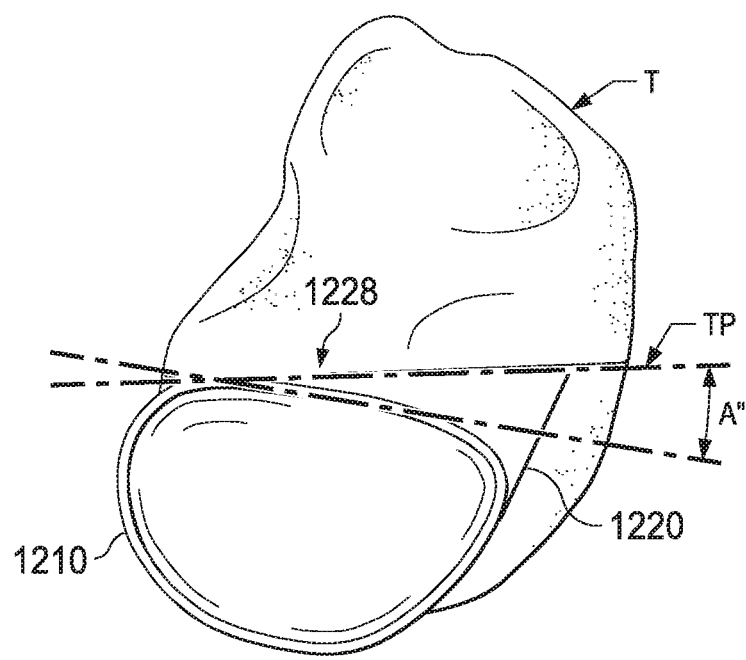

Referring now to FIGS. 16C and 17C, continued rotation of the femur with respect to the tibia results in angle $\alpha''$ which is greater than angle $\alpha'$. The PMD is now engaged with a third bearing surface of the natural femur having a different radius of curvature and a different portion of the TBC bearing surface 1226. As a result of this contact, the PMD 110 has translated posteriorly and is now spaced a distance D2" from the posterior surface 1250, which is greater than D2'. Additionally, the PMD 110 has rotated clockwise with respect to sidewall 1228 of the TBC represented by line TP to smaller angle A" which now a negative angle in comparison to the TP line. The illustrated relationship is position C. The PMD 110 has moved longitudinally, rotationally, and/or laterally between positions B and C, and positions A and C.

Figure 16D:
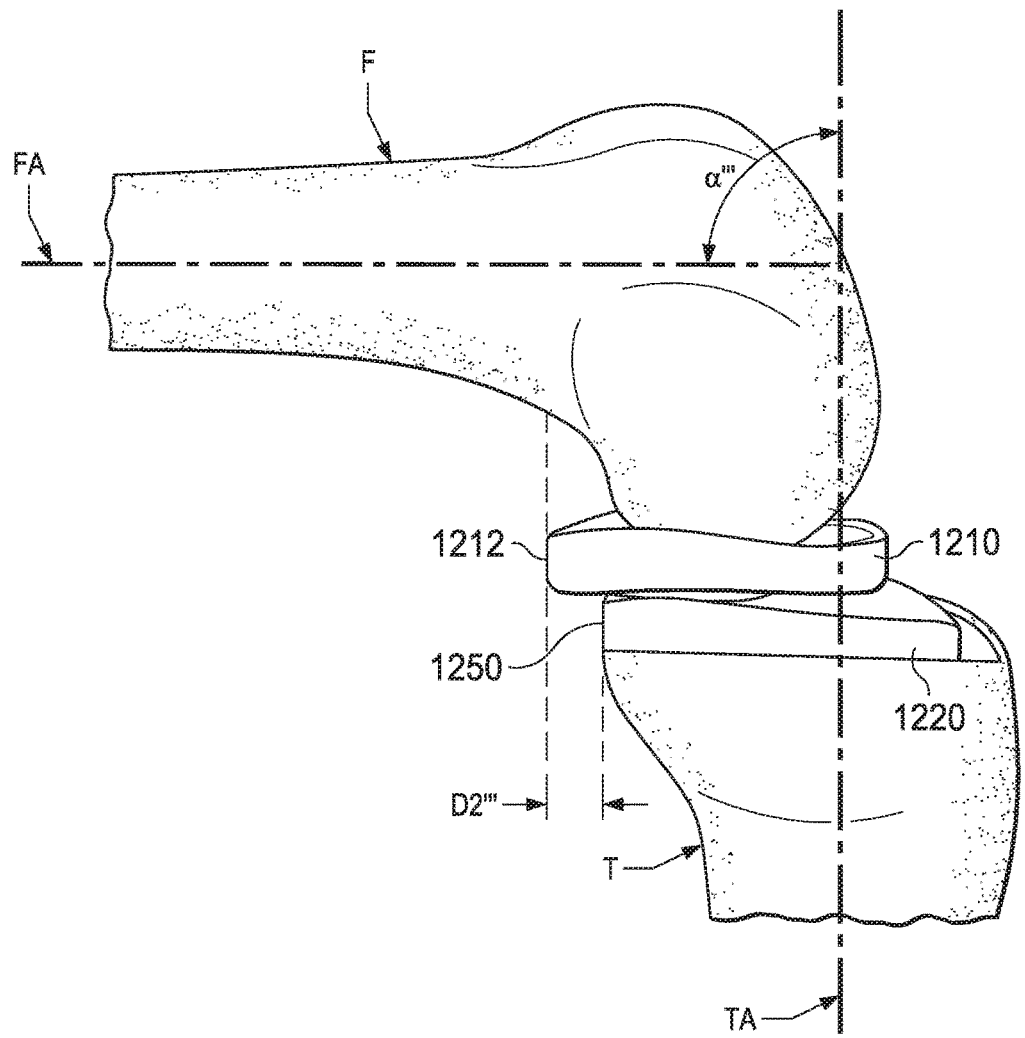

FIG. 16D illustrates that continued rotation of the femur with respect to the tibia to angle $\alpha'''$, which is substantially 90 degrees, results in further translation to a distance D2' which is greater than D2".

While the foregoing are not limiting, the PMD total translation distance D2 can range from 3-20 mm in the anterior to posterior plane, with one embodiment having D2' of 3 mm, D2" of 7 mm and D2''' of 14 mm. Similarly, the PMD rotational angle can range, without limitation, from 3 to 30 degrees of total angular rotation. With respect to the embodiment shown in FIGS. 10A-10C, angle A is approximately 10 degrees, angle A' is approximately 3 degrees, and angle A" is approximately −10 degrees from the TP line.

Although described in the context of a partial unicompartmental knee replacement system, the composite implants described above may be utilized for forming a variety of prosthetic devices. For example, in some instances the composite implants are utilized for knee joints (including meniscus and total knee joints), hip joints (including acetabular cups), shoulder joints, elbow joints, finger joints, and other load and/or non-load receiving prosthetic devices.

It should be appreciated that in some instances the prosthetic devices of the present disclosure are formed by other processes than those described herein. These manufacturing processes include any suitable manufacturing method. For example, without limitation any of the following manufacturing methods may be utilized: injection molding including inserting inserts; compression molding including inserting inserts; injection-compression molding including inserting inserts; compression molding of prefabricated elements preformed by any of the above methods including inserting inserts; spraying including inserting inserts; dipping including inserting inserts; machining from stocks or rods; machining from prefabricated elements including inserting inserts; and/or any of the above methods without inserts. Further, it should be appreciated that in some embodiments the prosthetic devices of the present disclosure are formed of medical grade materials other than those specifically identified above. In that regard, in some embodiments the prosthetic devices are formed of any suitable medical grade material.

While the principles of the present disclosure have been set forth using the specific embodiments discussed above, no limitations should be implied thereby. Any and all alterations or modifications to the described devices, instruments, and/or methods, as well as any further application of the principles of the present disclosure that would be apparent to one skilled in the art are encompassed by the present disclosure even if not explicitly discussed herein. It is also recognized that various presently unforeseen or unanticipated alternatives, modifications, and variations of the present disclosure may be subsequently made by those skilled in the art. All such variations, modifications, and improvements that would be apparent to one skilled in the art to which the present disclosure relates are encompassed by the following claims.

What is claimed is:

1. A partial unicompartmental knee replacement system for implantation between a femur and a tibia of a patient, comprising:
    a femoral component configured for resurfacing at least a portion of a femoral condyle, the femoral component having a first bearing surface with a first radius of curvature, a second bearing surface with a second radius of curvature, and a third bearing surface with a third radius of curvature; and
    a flexible meniscus component having a substantially ellipsoidal shape and configured for placement between the femoral component and the natural tibia without using any attachment means to keep the meniscus component in place, the meniscus component comprising an upper bearing surface for engaging the femoral component, a lower tibial-contacting bearing surface for directly engaging a native tibial plateau of the tibia, an outer body portion, and a central body portion, wherein the meniscus component floats in the knee joint between the tibia and the femoral component and during knee flexion: has a first position in the knee joint with respect to the tibia when the upper bearing surface is in contact with the first bearing surface of the femoral component, a second position in the knee joint with respect to the tibia when the upper bearing surface is in contact with the second bearing surface of the femoral component; and a third position in the knee joint with respect to the tibia when the upper bearing surface is in contact with the third bearing surface of the femoral component,
    wherein in the second position the meniscus component has translated posteriorly and is rotationally offset with respect to the first position, and wherein in the third position the meniscus component has further translated posteriorly and is rotationally offset with respect to the second position,
    wherein the floating meniscus component is configured to cooperate with the femoral component to move through a plurality of translational and rotational positions as the knee rotates through a variety of angles,
    wherein the outer body portion comprises an increased thickness and height relative to the central body portion, and wherein the outer body portion is sized and shaped to prevent unwanted expulsion of the meniscus component from the knee joint, and
    wherein the first, second, and third bearing surfaces of the femoral component have different radii of curvature.

2. The system of claim 1, wherein the first position is rotationally offset from at least one of the second and third positions.

3. The system of claim 1, wherein the first position is longitudinally offset from at least one of the second and third positions.

4. The system of claim 1, wherein the first position is laterally offset from at least one of the second and third positions.

5. The system of claim 1, wherein rotation of the meniscus component is greater than 2.5 degrees.

6. The system of claim 1, wherein translation of the meniscus component is greater than 5 mm.

7. The system of claim 5, wherein the translation of the meniscus component is greater than 5 mm.

* * * * *